(12) United States Patent
Taylor

(10) Patent No.: US 8,158,933 B2
(45) Date of Patent: Apr. 17, 2012

(54) DETECTOR APPARATUS AND PRE-CONCENTRATOR

(75) Inventor: Stephen John Taylor, Hyde Heath (GB)

(73) Assignee: Smiths Detection-Watford Limited, Hertfordshire (GB)

( * ) Notice: Subject to any disclaimer, the term of this patent is extended or adjusted under 35 U.S.C. 154(b) by 247 days.

(21) Appl. No.: 12/521,546

(22) PCT Filed: Dec. 10, 2007

(86) PCT No.: PCT/GB2007/004713
§ 371 (c)(1),
(2), (4) Date: Jun. 26, 2009

(87) PCT Pub. No.: WO2008/074987
PCT Pub. Date: Jun. 26, 2008

(65) Prior Publication Data
US 2010/0012833 A1   Jan. 21, 2010

(30) Foreign Application Priority Data
Dec. 20, 2006   (GB) .................................. 0625481.7

(51) Int. Cl.
*G01N 1/28* (2006.01)
*H01J 49/00* (2006.01)
*B01D 59/44* (2006.01)

(52) U.S. Cl. ........ 250/288; 250/287; 250/281; 250/397; 250/428; 73/863.23; 436/178

(58) Field of Classification Search .................. 250/288, 250/281, 287, 397, 428; 73/863.23; 436/178
See application file for complete search history.

(56) References Cited

U.S. PATENT DOCUMENTS

| | | | |
|---|---|---|---|
| 3,107,966 | A | 10/1963 | Bonhomme |
| 3,461,285 | A | 8/1969 | Werner et al. |
| 3,470,527 | A | 9/1969 | Bonhomme |
| 3,787,681 | A | 1/1974 | Brunnee et al. |
| 4,378,499 | A | 3/1983 | Spangler et al. |
| 4,551,624 | A | 11/1985 | Spangler et al. |
| 5,083,019 | A | 1/1992 | Spangler |
| 5,227,628 | A | 7/1993 | Turner |
| 5,304,797 | A | 4/1994 | Irie et al. |
| 5,574,277 | A | 11/1996 | Taylor |
| 5,723,861 | A | 3/1998 | Carnahan et al. |
| 5,854,431 | A | 12/1998 | Linker et al. |
| 5,952,652 | A | 9/1999 | Taylor et al. |
| 6,051,832 | A | 4/2000 | Bradshaw |
| 6,073,498 | A | 6/2000 | Taylor |
| 6,102,746 | A | 8/2000 | Nania et al. |
| 6,225,623 | B1 | 5/2001 | Turner et al. |
| 6,239,428 | B1 | 5/2001 | Kunz |

(Continued)

FOREIGN PATENT DOCUMENTS
EP   0135747   4/1985
(Continued)

*Primary Examiner* — Nikita Wells
(74) *Attorney, Agent, or Firm* — Reinhart Boerner Van Deuren s.c.

(57) ABSTRACT

An IMS detector has a pin-hole or capillary inlet having a coating of an adsorbent material, such as polydimethylsiloxane, which is adsorbent to an analyte substance of interest. The analyte is adsorbed into the material until a heater is energized to heat the adsorbent material and release the adsorbed analyte substance for detection in a detector.

24 Claims, 1 Drawing Sheet

U.S. PATENT DOCUMENTS

| | | |
|---|---|---|
| 6,442,997 B1 | 9/2002 | Megerle |
| 6,459,079 B1 | 10/2002 | Machlinski et al. |
| 6,481,263 B1 | 11/2002 | Haley |
| 6,495,824 B1 | 12/2002 | Atkinson |
| 6,502,470 B1 | 1/2003 | Taylor et al. |
| 6,523,393 B1 | 2/2003 | Linker et al. |
| 6,825,460 B2 | 11/2004 | Breach et al. |
| 7,098,449 B1 | 8/2006 | Miller et al. |
| 7,118,712 B1 * | 10/2006 | Manginell et al. ............... 422/69 |
| 7,311,566 B2 | 12/2007 | Dent |
| 2002/0150923 A1 * | 10/2002 | Malik .............................. 435/6 |
| 2004/0259265 A1 | 12/2004 | Bonne |
| 2005/0017163 A1 | 1/2005 | Miller et al. |
| 2005/0095722 A1 | 5/2005 | McGill et al. |
| 2005/0161596 A1 | 7/2005 | Guevremont et al. |
| 2005/0178975 A1 | 8/2005 | Glukhoy |
| 2005/0253061 A1 | 11/2005 | Cameron et al. |
| 2006/0249673 A1 | 11/2006 | Breach et al. |
| 2009/0090196 A1 * | 4/2009 | Clark et al. ................. 73/863.12 |
| 2010/0012834 A1 * | 1/2010 | Taylor ........................... 250/287 |
| 2010/0015722 A1 * | 1/2010 | Taylor ........................... 436/181 |
| 2010/0317125 A1 * | 12/2010 | Taylor ........................... 436/181 |

FOREIGN PATENT DOCUMENTS

| | | |
|---|---|---|
| GB | 2323165 | 9/1998 |
| WO | WO 9301485 | 1/1993 |
| WO | WO 9322033 | 11/1993 |
| WO | WO 9921212 | 4/1999 |
| WO | WO 0079261 | 12/2000 |
| WO | WO 0195999 | 12/2001 |
| WO | WO 02078047 | 10/2002 |
| WO | WO 2004012231 | 2/2004 |
| WO | WO 2006046077 | 5/2006 |
| WO | WO 2008035095 | 3/2008 |

* cited by examiner

DETECTOR APPARATUS AND PRE-CONCENTRATOR

This application is related to three other concurrently filed copending patent applications, namely U.S. patent application Ser. No. 11/918,940, entitled "Detection Apparatus," U.S. patent application Ser. No. 12/521,537, entitled "Detection Apparatus," and U.S. patent application Ser. No. 12/521,549, entitled "Gas Preconcentrator for Detection Apparatus," all assigned to the assignee of the present patent application, which three patent applications are hereby incorporated herein by reference.

BACKGROUND OF THE INVENTION

Field of the Invention

This invention relates to detector apparatus of the kind having an inlet in the form of a pin-hole or capillary passage by which an analyte substance is admitted to the interior of the detector and to preconcentrators.

Ion mobility spectrometers or IMS apparatus are often used to detect substances such as explosives, drugs, blister and nerve agents, or the like. An IMS apparatus typically includes a detector cell to which a sample of air containing a suspected substance or analyte is continuously supplied as a gas or vapor. The cell operates at or near atmospheric pressure and contains electrodes energized to produce a voltage gradient along the cell. Molecules in the sample of air are ionized, such as by means of a radioactive source, UV source, or by corona discharge, and are admitted into the drift region of the cell by an electrostatic gate at one end. The ionized molecules drift to the opposite end of the cell at a speed dependent on the mobility of the ions. By measuring the time of flight along the cell, it is possible to identify the ions. Where the sample analyte is only present in small concentrations in the sample gas, there can be a relatively low signal-to-noise ratio and this can make reliable detection very difficult. It is known to use a preconcentrator at the inlet in order to produce a bolus of sample with increased levels of analyte. The preconcentrator contains an adsorbent material to which the analyte substance in gas supplied to the preconcentrator binds during an adsorption phase. The preconcentrator is subsequently heated to cause the analyte substance to be desorbed as a bolus of gas with an increased concentration of analyte. Other forms of detector also make use of preconcentrators.

It is desirable to provide alternative detector apparatus and preconcentrators.

SUMMARY OF THE INVENTION

According to one aspect of the present invention there is provided detector apparatus of the above-specified kind, characterized in that the surface of the pin-hole or capillary passage over which the analyte substance flows consists at least in part of an adsorbent material, and that the detector apparatus is arranged and configured to cause the adsorbent material to desorb adsorbed substance on demand.

The adsorbent material may be a coating on the surface of the pin-hole or capillary passage. The adsorbent material may include polydimethylsiloxane. The apparatus preferably includes a heater by which the adsorbent material is caused to desorb an adsorbed substance. The apparatus may be an IMS apparatus, with the pin-hole or capillary passage opening to a reaction region that is arranged to ionize admitted analyte molecules, and a reaction region that is arranged to supply the ionized molecules to a drift region for detection. The apparatus may include a plurality of inlets, each of which has a pin-hole or capillary passage with a surface consisting at least in part of an adsorbent material.

According to another aspect of the present invention there is provided a preconcentrator for a detector apparatus, with the preconcentrator being arranged to adsorb analyte substance and to release the adsorbed substance on demand, characterized in that the preconcentrator has an adsorbent surface providing a pin-hole or capillary passage, and that the preconcentrator is arranged to provide an inlet to the detector apparatus.

The adsorbent surface is preferably made of polydimethylsiloxane.

DESCRIPTION OF THE DRAWINGS

An IMS detector apparatus including a preconcentrator inlet that is constructed and operated according to the present invention will now be described, by way of example, with reference to the accompanying drawings, in which.

DETAILED DESCRIPTION OF THE PREFERRED EMBODIMENT

Figure 1:
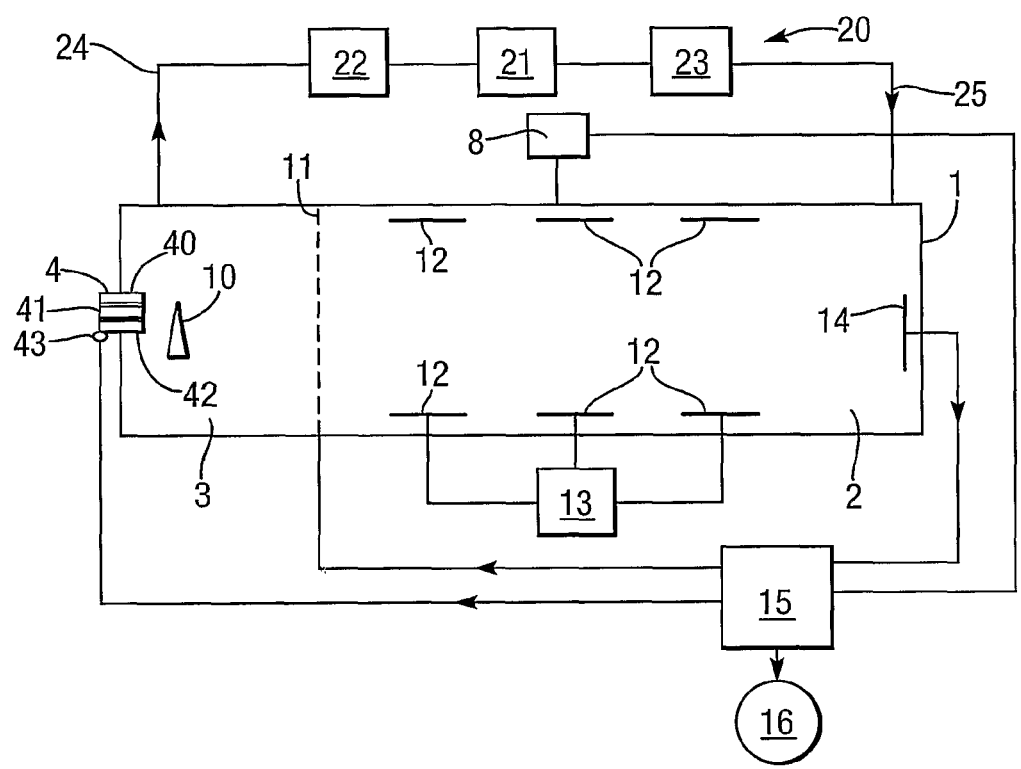
FIG. 1 shows an IMS apparatus schematically.

With reference first to FIG. 1, the apparatus takes the form of an ion mobility spectrometer ("IMS") having a generally tubular housing 1 with an analysis or drift region 2 towards its right-hand end (as shown in FIG. 1) and an ionization or reaction region 3 towards its opposite left-hand end (as shown in FIG. 1).

An inlet 4 at the left-hand end of the housing 1 (as shown in FIG. 1) opens into the interior of the reaction region 3 so that molecules of interest can pass from outside into the reaction region 3. The inlet 4 will be described in detail later.

The reaction region 3 contains apparatus to ionize molecules of the analyte substance, such as a corona discharge point 10, at a high potential. The reaction region 3 and the drift region 2 are both at atmospheric pressure or just slightly below atmospheric pressure. The reaction region 3 and the drift region 2 may be separated from one another by an optional, conventional electrostatic shutter 11 such as a Bradbury Nielson gate by which the flow of ions into the drift region 2 may be controlled. The drift region 2 has a series of pairs of electrodes 12 on opposite sides thereof which are longitudinally spaced from one another along the length of the drift region 2. A voltage supply 13 applies a voltage to each electrode pair 12, which voltage increases from the left to the right along the length of the drift region 2 (as shown in FIG. 1) so that ions passed by the electrostatic shutter 11 are subject to a voltage gradient, which draws them along the length of the drift region 2. A collector plate 14 mounted at the far, right-hand end of the drift region 2 (as shown in FIG. 1) collects ions after passage along the drift region 2. The charge produced by each ion when it impacts the collector plate 14 is supplied as an electrical signal to a processor unit 15. The processor unit 15 analyzes the signals to produce spectra representative of the mobility of the different ions detected and supplies these to a display or other utilization apparatus 16.

A gas flow system 20 provides a flow of clean dry air along the inside of the housing 1 against the flow of the ions. The gas flow system includes a pump 21 with molecular sieve inlet and outlet filters 22 and 23 respectively located at its inlet and outlet. The inlet filter 22 connects with an inlet pipe 24, which opens into the housing 1 towards the inlet end of the reaction region 3 (shown on the left end in FIG. 1) The outlet filter 23 connects with an outlet pipe 25, which opens into the housing 1 towards the downstream end of the drift region 2 (shown on the right end in FIG. 1). The pump 21 operates to draw gas from the reaction region 3 so that it flows through the first filter 22, the pump 21 and the second filter 23 before flowing back into the housing 1 at the right-most end of the drift region 2 (as shown in FIG. 1). A pressure pulser 8, which may be an electromagnetic transducer similar to a loudspeaker, may be connected to the interior of the housing 1 in the manner described in U.S. Pat. No. 6,073,498, to Taylor et al., which is hereby incorporated herein by reference, to draw the analyte substance into the housing 1 via the inlet 4. As so far described, the apparatus is relatively conventional.

The inlet 4 differs from conventional inlets in that it is provided by a capillary tube 40 with an axial passage or bore 41 having a coating of an adsorbent material 42 that will adsorb the analyte substance of interest. Typically, the diameter of the bore 41 is approximately 0.5 mm (it is not shown to scale in the drawings), and the material used for the coating of the adsorbent material 42 may be polydimethylsiloxane. The coating of adsorbent material 42, therefore, forms the surface over which all of the sample inlet gas flows as it enters into the reaction region 3. It is not essential, however, that the adsorbent surface be provided by a coating thereupon, since it could alternatively be provided by a coating of adsorbent material on a tube or sleeve located within the inlet 4. Alternatively, the inlet 4 (or the tube or sleeve) could be made entirely of the adsorbent material 42 instead of being coated with it. The inlet 4 also includes a heater 43 that is connected to be operated by the processor unit 15 and by which the temperature of the adsorbent material 42 can be raised on demand as necessary.

In operation, the detector apparatus initially functions in an adsorption phase in which no heat is applied to the inlet 4, so that most of the analyte substance of interest is adsorbed by the adsorbent material 42. After a set time, the apparatus starts a desorption phase during which the processor unit 15 energizes the heater 43 to increase the temperature of the adsorbent material 42 and thereby cause the adsorbed analyte substance to be driven off as a bolus or concentrated burst into the reaction region 3. This momentary high concentration of the analyte substance enables greater numbers of analyte ions to be produced, and produces spectra with an increased signal-to-noise ratio.

Locating the preconcentrator adsorbent material 42 in the inlet 4 itself ensures intimate contact of the inlet gas with the adsorbent material 42. This leads to an efficient adsorption. It also enables the bulk of the adsorbent material to be minimized, leading to rapid thermal cycling and reduced energy consumption, which can be important in battery-powered devices.

Figure 2:
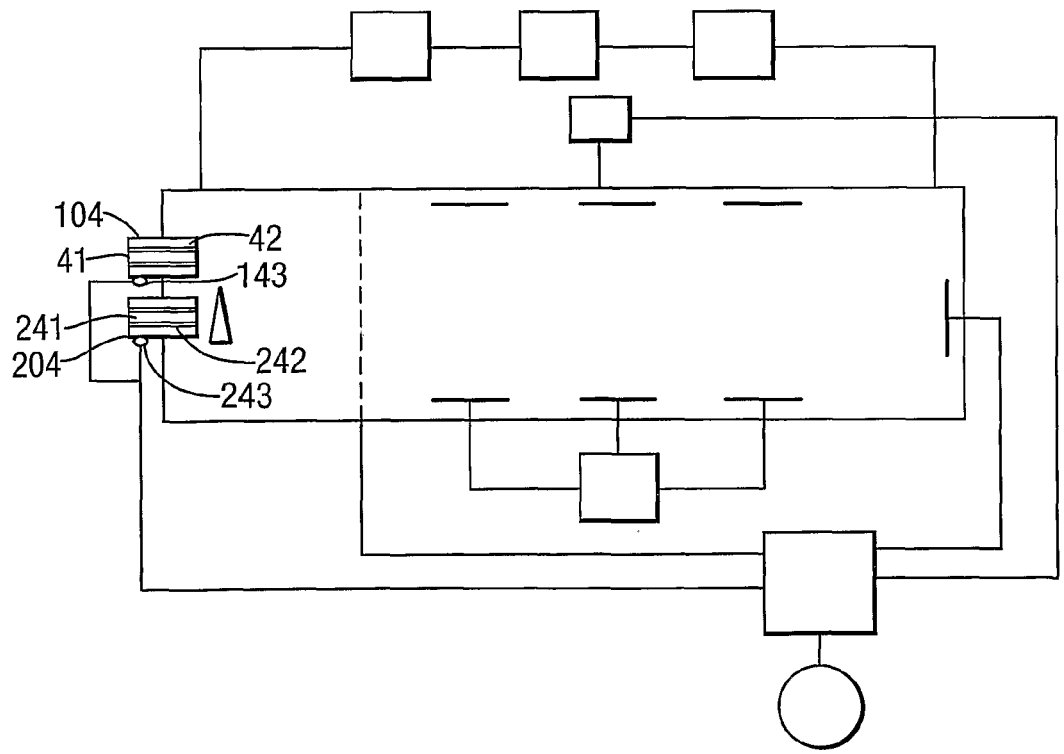
FIG. 2 shows a modification of the IMS apparatus of FIG. 1.

If a single inlet 4 does not allow for sufficient flow of analyte substance into the detector it would be possible to have more than one inlet in the manner shown in FIG. 2. In this arrangement two inlets 104 and 204 are mounted side-by-side to form parallel entry paths into the reaction region. In other respects, the apparatus shown in FIG. 2 is that same as that shown in FIG. 1 (and thus elements in FIG. 2 that are identical to the elements of FIG. 1 are not provided with reference numerals).

The invention is particularly useful in IMS apparatus, but may also have application in different forms of detector.

Although the foregoing description of the present invention has been shown and described with reference to particular embodiments and applications thereof, it has been presented for purposes of illustration and description and is not intended to be exhaustive or to limit the invention to the particular embodiments and applications disclosed. It will be apparent to those having ordinary skill in the art that a number of changes, modifications, variations, or alterations to the invention as described herein may be made, none of which depart from the spirit or scope of the present invention. The particular embodiments and applications were chosen and described to provide the best illustration of the principles of the invention and its practical application to thereby enable one of ordinary skill in the art to utilize the invention in various embodiments and with various modifications as are suited to the particular use contemplated. All such changes, modifications, variations, and alterations should therefore be seen as being within the scope of the present invention as determined by the appended claims when interpreted in accordance with the breadth to which they are fairly, legally, and equitably entitled.

What is claimed is:

1. A detector apparatus comprising:
   an inlet in the form of a pin-hole or capillary passage by which an analyte substance is admitted to the interior of the detector apparatus;
   wherein the surface of the pin-hole or capillary passage over which the analyte substance flows is comprised at least in part of an adsorbent material; and
   wherein the detector is arranged and configured to cause the adsorbent material to desorb adsorbed analyte substance upon demand in a bolus.

2. The detector apparatus defined in claim 1, wherein the adsorbent material comprises:
   a coating on the surface of the pin-hole or capillary passage.

3. The detector apparatus defined in claim 1, wherein the adsorbent material comprises polydimethylsiloxane.

4. The detector apparatus defined in claim 1, wherein the detector apparatus further comprises:
   a heater by the operation of which the adsorbent material is caused to desorb adsorbed substance.

5. The detector apparatus defined in claim 1, wherein the detector apparatus comprises an ion mobility spectrometer apparatus, wherein the pin-hole or capillary passage opens to a reaction region arranged and configured to ionize admitted analyte molecules, and wherein the reaction region is arranged and configured to supply the ionized molecules to a drift region for detection.

6. The detector apparatus defined in claim 1, wherein the detector apparatus comprises:
   a plurality of inlets, wherein each inlet has a pin-hole or capillary passage with a surface comprised at least in part of an adsorbent material.

7. The detector apparatus defined in claim 1, wherein the pin-hole or capillary passage is arranged and configured to adsorb an analyte substance contained in a sample of air.

8. A preconcentrator for a detector apparatus, the preconcentrator being arranged and configured to adsorb an analyte substance and to release the adsorbed analyte substance on demand in a bolus, wherein the preconcentrator has an adsorbent surface providing a pin-hole or capillary passage, and wherein the preconcentrator is arranged and configured to provide an inlet to the detector apparatus.

9. The preconcentrator as defined in claim 8, wherein the adsorbent surface comprises polydimethylsiloxane.

10. The detector apparatus defined in claim 8, wherein the preconcentrator is arranged and configured to adsorb an analyte substance contained in a sample of air.

11. A detector apparatus comprising:
- a housing having a first end at which an analyte gas or vapor will be admitted to the housing and a second end opposite the first end;
- a reaction region located in the housing adjacent the first end thereof;
- a drift region located in the housing between the reaction region and the second end of the housing; and
- an inlet in the form of a pin-hole or capillary passage by which an analyte substance is admitted to the reaction region;

wherein the surface of the pin-hole or capillary passage over which the analyte substance flows is comprised at least in part of an adsorbent material; and wherein the inlet is arranged and configured to cause the adsorbent material to desorb adsorbed analyte substance upon demand in a bolus.

12. The detector apparatus defined in claim 11, wherein the adsorbent material comprises:
- a coating on the surface of the pin-hole or capillary passage.

13. The detector apparatus defined in claim 11, additionally comprising:
- a tube or sleeve located within the inlet;

wherein the adsorbent material comprises:
- a coating on the surface of the tube or sleeve.

14. The detector apparatus defined in claim 11, additionally comprising:
- a tube or sleeve located within the inlet;

wherein the tube or sleeve is made of the adsorbent material.

15. The detector apparatus defined in claim 11, wherein the adsorbent material comprises:
- a coating on the surface of the inlet.

16. The detector apparatus defined in claim 11, wherein the inlet is made of the adsorbent material.

17. The detector apparatus defined in claim 11, wherein the adsorbent material comprises polydimethylsiloxane.

18. The detector apparatus defined in claim 11, additionally comprising:
- a heater by the operation of which the adsorbent material is caused to desorb adsorbed substance.

19. The detector apparatus defined in claim 11, additionally comprising:
- at least one additional inlet in the form of a pin-hole or capillary passage by which an analyte substance is admitted to the reaction region;

wherein the surface of the pin-hole or capillary passage of the at least one additional inlet over which the analyte substance flows is comprised at least in part of an adsorbent material; and wherein the at least one additional inlet is arranged and configured to cause the adsorbent material to desorb adsorbed substance upon demand.

20. The detector apparatus defined in claim 11, additionally comprising:
- an ionizing apparatus located in the reaction region that ionizes molecules of the analyte gas or vapor that has been admitted to the reaction region.

21. The detector apparatus defined in claim 11, additionally comprising:
- an electrostatic shutter that controls the flow of ions from the reaction region to the drift region.

22. The detector apparatus defined in claim 11, additionally comprising:
- a plurality of longitudinally spaced-apart electrode pairs located in the drift region that establish an electrical field in the drift region which draws ions located in the drift region in a direction from the first end of the housing to the second end of the housing.

23. The detector apparatus defined in claim 11, additionally comprising:
- a collector plate located near the second end of the housing, the collector plate collecting ions passing to the second end of the housing and providing an output to a processor indicative of the ions detected by the collector plate.

24. The detector apparatus defined in claim 11, wherein the pin-hole or capillary passage is arranged and configured to adsorb an analyte substance contained in a sample of air.

* * * * *

UNITED STATES PATENT AND TRADEMARK OFFICE
CERTIFICATE OF CORRECTION

PATENT NO. : 8,158,933 B2
APPLICATION NO. : 12/521546
DATED : April 17, 2012
INVENTOR(S) : Stephen John Taylor It is certified that error appears in the above-identified patent and that said Letters Patent is hereby corrected as shown below:

In the specification:
Column 2, line 17
"An IMS detector apparatus including a preconcentrator" should read --An IMS detector apparatus including a pre-concentrator--.

Signed and Sealed this
Third Day of July, 2012

David J. Kappos
*Director of the United States Patent and Trademark Office*